United States Patent [19]

Naegeli

[11] 4,046,716

[45] Sept. 6, 1977

[54] NOVEL ODORANT COMPOSITIONS

[75] Inventor: Peter Naegeli, Wettingen, Switzerland

[73] Assignee: Givaudan Corporation, Clifton, N.J.

[21] Appl. No.: 716,724

[22] Filed: Aug. 23, 1976

Related U.S. Application Data

[62] Division of Ser. No. 569,121, April 17, 1975, Pat. No. 4,010,213.

[51] Int. Cl.$^2$ ............................................. C11B 9/00
[52] U.S. Cl. ................................ 252/522; 260/617 R
[58] Field of Search ..................... 252/522; 260/617 R

[56] References Cited

U.S. PATENT DOCUMENTS

| | | | |
|---|---|---|---|
| 3,268,589 | 8/1966 | Rowland et al. | 260/617 R |
| 3,899,597 | 8/1975 | Mookherjee | 260/617 R |
| 4,010,213 | 3/1977 | Naegeli | 252/522 |

OTHER PUBLICATIONS

Milas et al. J. Amer. Chem. Soc. 70, pp. 1584-1591. 1948.

*Primary Examiner*—Veronica O'Keefe
*Attorney, Agent, or Firm*—Thomas Cifelli, Jr.; Robert F. Tavares

[57] ABSTRACT

Novel odorants of the formulae:

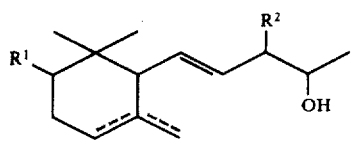

(I)

and

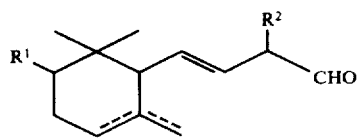

(II)

wherein $R^1$ represents a hydrogen atom or a methyl group and $R^2$ represents a $C_{1-6}$ alkyl group and wherein one of the two additional bonds indicated by dots may be present.

6 Claims, No Drawings

NOVEL ODORANT COMPOSITIONS

This is a division of application Ser. No. 569,121 filed Apr. 17, 1975, now U.S. Pat. No. 4,010,213.

FIELD OF THE INVENTION

This invention relates to novel alcohols and aldehydes, and to novel odorant compositions containing them.

SUMMARY OF THE INVENTION

The novel odorants have the formulae I and II, supra.

The alcohols of formula I hereinbefore are manufactured by reacting an aldehyde of the general formula

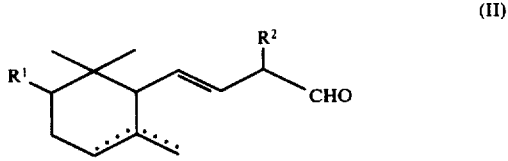

(II)

wherein $R^1$, $R^2$ and the dotted lines have the significance given earlier, with a metal-organic compound of the formula A—$CH_3$, wherein A represents an alkali metal or a grouping Hal—Mg— in which Hal represents a chlorine, bromine or iodine atom, and hydrolysing the reaction product.

The aldehydes of formula II can be prepared according to methods known per se; for example, by a glycidic ester condensation according to Darzens-Erlenmeyer-Claisen from ketones of the general formula

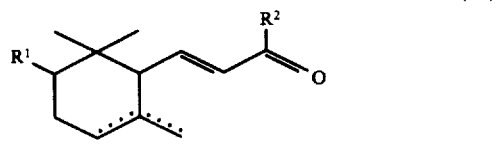

(III)

wherein $R^1$, $R^2$ and the dotted lines have the significance given earlier.

DESCRIPTION OF THE PREFERRED EMBODIMENTS

The reaction of an aldehyde of formula II with a metal-organic compound aforesaid and the hydrolysis of the reaction product can be carried out in accordance with methods known per se.

Preferred alcohols of formula I are:

3-methyl-5-(2,6,6-trimethyl-2-cyclohexyenyl)-4-penten-2-ol,
3-methyl-5-(2,5,6,6-tetramethyl-2-cyclohexenyl)-4-penten-2-ol,
3-methyl-5-(2,2,6-trimethylcyclohexyl)4-penten-2-ol,
3-methyl-5-(2,2-diemthyl-6-methylenecyclo-hexyl)-4-penten-2-ol and
3-ethyl-5-(2,6,6-trimethyl-2-cyclohexenyl)-4-penten-2-ol, which can be manufactured according to the present process from the corresponding aldehydes, namely from:

2-methyl-4-(2,6,6-trimethyl-2-cyclohexenyl)-3-butenal,
2-methyl-4-(2,5,6,6-tetramethyl-2-cyclohexenyl)-3-butenal,
2-methyl-4-(2,2,6-trimethylcyclohexyl)-3-butenal,
2-methyl-4-(2,2,-dimethyl-6-methylenecyclohexyl)-3-butenal and
2-ethyl-4-(2,6,6-trimethyl-2-cyclohexenyl)-3-butenal.

The alcohols of formula I possess particular odorant properties, being characterised by an especially fine sandalwood note. Such an odorant note has hitherto been completely unknown in the ionone series (i.e. in compounds such as those of formula I). The alcohols of formula I can accordingly be used as odorants. Since sandalwood oil is a very valuable and indispensable ingredient in perfumery and is becoming increasingly scarce and thus inexpensive, there exists a great need for suitable substitutes. The alcohols provided by the present invention are, to a large extent, capable of replacing sandalwood oil in perfumery and cosmetics. They are suitable for the manufacture of perfume compositions and Eau de Cologne, to which they often impart a reasonable note in amounts of about 0.1–40 wt.%, and also for perfuming technical and cosmetic products of all kinds (e.g. soaps, solid and liquid detergents, bath additives, lotions, creams, powders, deodorants etc) in weight ratios of 1 part per million to about 6%; it being understood, however, that these amounts may be increased or decreased as desired.

It will accordingly be appreciated that the invention includes within its scope a. an odorant composition which contains as an essential odour-imparting ingredient an alcohols of formula I hereinbefore, and b. a method of imparting an odour to materials by applying thereto or incorporating therein an odour-imparting amount of an odorant composition as defined under (a) or of an alcohol of formula I hereinbefore.

The aldehyde starting materials of formula II are novel and also form part of the present invention. These aldehydes likewise possess odorant properties as well as aroma properties.

The aldehydes of formula II can be prepared according to methods know per se; for example, by a glycidic ester condensation according to Darzens-Erlenmeyer-Claisen from ketones of the general formula

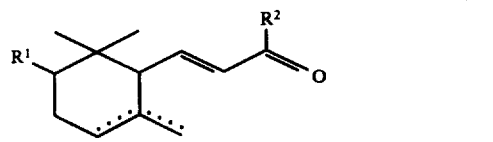

(III)

wherein $R^1$, $R^2$ and the dotted lines have the significance given earlier.

A ketone of formula III is condensed with a haloacetic acid ester in the presence of an alkaline condensation agent to give a glycidic ester, which is then converted into the free acid by careful hydrolysis and decarboxylated.

The aldehydes of formula II can also be prepared by reacting a ketone of formula III in a manner known per se [see J. Am. Soc. 84, 3782 (1962); Tetrahedron Letters, 1963 169 and J. Am. Soc. 87, 1353 (1965)] with a sulphur compound of the formula

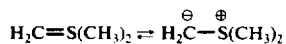

to give an epoxide of the general formula

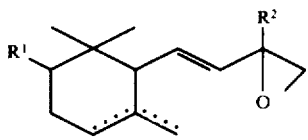

wherein $R^1$, $R^2$ and the dotted lines have the significance given earlier, and isomerising said epoxide by treatment with a weak Lewis acid such as lithium perchlorate in an aprotic solvent, preferably an ether such as tetrahydrofuran, dioxane or 1,2-dimethoxyethane.

The following Examples illustrate the present invention:

EXAMPLE 1

A mixture of 192 g of α-ionone, 165.4 g of ethyl chloroacetate, 500 mg of phenothiazine and 100 ml of pyridine is treated with 81 g of sodium methylate within 30 minutes at −10° C to −15° C with the exclusion of moisture and oxygen from the air. After the addition of 100 ml of absolute ether, the mixture is stirred for 4 hours at −5° C and treated with 400 ml of 15% methanolic sodium hydroxide while cooling. The mixture is stirred for 1 hour at 10° C, cooled to −30° C and adjusted to a pH of about 4 by the addition of 600 ml of glacial acetic acid. After warming to room temperature, 1 liter of water is added and the mixture stirred again for 15 minutes ($CO_2$ evolution). Extraction with hexane, washing the organic phase neutral, drying over anhydrous sodium sulphate and removal of the solvent under reduced pressure yields 190 g of a brown, liquid crude product which is subjected to fractional distillation in vacuo and produces 125 g of 2-methyl-4-(2,6,6-trimethyl-2-cyclohexenyl)-3-butenal; b.p.$_{0.15}$ = 90° C; $n_D^{20}$ = 1.4880. Odour: woody, ionone-like, flowery.

EXAMPLE 2

A solution of methylmagnesium iodide, prepared from 11 g of magnesium shavings and 76 g of methyl iodide, in 700 ml of absolute ether is added dropwise at −10° C under nitrogen to a solution of 62 g of 2-methyl-4-(2,6,6-trimethyl-2-cyclohexenyl)-3-butenal in 700 ml of ether. The mixture is stirred for 4 hours at 30° C and then poured on to an excess of ice-cold ammonium chloride solution. The mixture is extracted with ether in the usual manner, the extract is washed neutral with water and dried over anhydrous sodium sulphate to give, after removal of the solvent, 66 g of a yellow, slightly viscous oil which, after distillation in vacuo, yields 52 g of 3-methyl-5-(2,6,6-trimethyl-2-cyclohexenyl)-4-penten-2-ol; b.p.$_{0.008}$ = 90°; $n_D^{20}$ = 1.4890. This alcohol has a very fine, tenacious sandalwood odour.

EXAMPLE 3

In a manner analogous to that described in Examples 1 and 2, the following compounds were obtained:

2-Methyl-4-(2,5,6,6-tetramethyl-2-cyclohexenyl)-3-butenal; b.p.$_{0.005}$ = 85° C;

IR (film): 2710, 1730, 1455, 1390/1380/1370, 1255, 985, 815 cm$^{-1}$.

Odour: flowery with slight fruity sub-note.

3-Methyl-5-(2,5,6,6-tetramethyl-2-cyclohexenyl)-4-penten-2-ol; b.p.$_{0.001}$ = 89° C; $n_D^{20}$ = 1.4920;

IR (film): 3380, 1455, 1390, 1380, 1365, 1215, 1090, 1000, 985, 940, 910, 810 cm$^{-1}$.

Odour: sandalwood-like.

2-Ethyl-4-(2,6,6-trimethyl-2-cyclohexenyl)-3-butenal

IR (film): 2700, 1730, 1455, 1385, 1365, 980, 830 cm$^{-1}$.

Odour: sandalwood-like, fig-like, reminiscent of ionone.

3-Ethyl-5-(2,6,6-trimethyl-2-cyclohexenyl)-4-penten-2-ol; b.p.$_{0.08}$ = 82° C; $n_D^{20}$ = 1.4929;

IR (film): 3350, 1460, 1385, 1370, 980 cm$^{-1}$.

Odour: sandela, sandalwood-like.

3-Methyl-5-(2,2,6-trimethylcyclohexyl)-4-penten-2-ol; b.p.$_{0.001}$ = 63° C; $n_D^{20}$ = 1.4810;

IR (film): 3450, 1450, 1380, 1370, 1360, 1085, 980, 930, 920, 900 cm$^{-1}$.

Odour: new, increased sandalwood note, flowery.

3-Methyl-5-(2,2-dimethyl-6-methylenecyclohexyl)-4-penten-2-ol;

IR (film): 3450, 1642, 1450, 1380, 1360, 1080, 980, 935, 925, 885 cm$^{-1}$.

Odour: mellow, clinging sandalwood note.

EXAMPLE 4

1.3 g of a 55–60% sodium hydride paste are freed from paraffin oil with pentane and then suspended in 50 ml of dry dimethyl sulphoxide. After stirring for 1 hour at 70° C there is obtained a clear solution to which, after cooling to room temperature, 30 ml of dry tetrahydrofuran are added. The mixture is cooled to 0° C and successively treated, each time over a period of 5 minutes, with a solution of 6.1 g of trimethylsulphonium iodide in 30 ml of dimethyl sulphoxide and 4.8 g of α-ionone in 10 ml of dimethyl sulphoxide. The resulting mixture is stirred for 15 minutes at 0° C and for 75 minutes at 35° C. For the working-up, the mixture is treated with ice-cold ammonium chloride solution and extracted with hexane. The extract is washed neutral, dried and concentrated to yield 4.8 g of a yellow oil from which, by vacuum distillation, there are obtained 4.0 g of 2-methyl-1,2-oxido-4-(2,6,6-trimethyl-2-cyclohexenyl)-3-butene; b.p.$_{0.005}$ = 80° C.

IR (film): 1450, 1380, 1360, 1295, 1202, 1130, 1070, 1060, 980, 965, 905, 895, 820, 808, 775, 740 cm$^{-1}$.

EXAMPLE 5

3.1 g of 2-methyl-1,2-oxido-4-(2,6,6-trimethyl-2-cyclohexenyl)-3-butene and 1.65 g of lithium perchlorate are stirred in 30 ml of dry 1,2-dimethoxyethane at 90° C for 60 minutes. The yellow solution is diluted with ether, washed with water, dried and concentrated under reduced pressure. There are obtained 3.1 g of 2-methyl-4-(2,6,6-trimethyl-2-cyclohexenyl)-3-butenal; b.p.$_{0.15}$ = 90° C; $n_D^{20}$ = 1.4880.

EXAMPLE 6

In a manner analogous to that described in Examples 4 and 5 the following compounds were obtained:

2-Methyl-4-(2,2,6-trimethylcyclohexyl)-3-butenal;

IR (film): 2730, 1730, 1455, 1385, 1375, 1365, 975 cm$^{-1}$.

Odour: camphorous, green, fresh, flowery, slightly woody.

2-Methyl-4-(2,2-dimethyl-6-methylenecyclohexyl)-3-butenal;

IR (film): 2740, 1730, 1645, 1455, 1385, 1365, 980, 970, 890 cm$^{-1}$.

Odour: woody, ionone-like, flowery.

The following Examples illustrate typical odorant compositions containing the alcohols of formula I or the aldehydes of formula II:

Example A

Odorant composition having a rose-sandalwood note.

| | Parts by weight |
|---|---|
| Geranium resinoid | 20 |
| Geranium oil | 20 |
| Cinnamic alcohol ex Storax | 50 |
| Geraniol savon | 110 |
| Linalool | 60 |
| Phenylethyl alcohol | 80 |
| Rosacetol Givaudan | 30 |
| Baccartol Givaudan | 100 |
| p-tertbutylcyclohexyl acetate | 130 |
| 3-Methyl-5-(2,6,6-trimethyl-2-cyclohexenyl)-4-penten-2-ol | 400 |
| | 1000 |

Compositions having the foregoing odorant note can be used for perfuming toilet soaps and shaving soaps or shaving creams.

Example B

| Odorant composition | Parts by weight |
|---|---|
| Basil oil * | 20 |
| Calamus oil * | 20 |
| Vanillin * | 10 |
| Lemon oil Italian | 40 |
| Jasmin absolu reconstitution | 40 |
| Lavender oil French | 70 |
| Bergamotte oil | 200 |
| Geranium oil | 25 |
| Methylnonylacetaldehyde * | 5 |
| p-Tertbutylcyclohexyl acetate | 80 |
| γ-Methylionone | 50 |
| Cedarwood oil American | 50 |
| Vetiver oil Bourbon | 20 |
| Patchouli oil | 20 |
| Petitgrain oil French | 50 |
| Heliotropin | 25 |
| Coumarin | 20 |
| Eugenol | 20 |
| Isobutylsalicylate | 30 |
| Oak-moss soluble | 5 |
| Incense resinoid | 10 |
| Musk ketone | 10 |
| 3-Methyl-5-(2,6,6-trimethyl-2-cyclohexenyl)-4-penten-2-ol | 180 |
| | 1000 |

* 10% in phthalic acid diethyl ester

This odorant composition as an Eau de Cologne like note in the direction of "Eau de Santal", such as is very popular in men's lines. The odour is fresh and lively, being reasonably balanced with the sandalwood note.

Example C

| Odorant composition | Parts by weight |
|---|---|
| Bornyl acetate liquid | 260 |
| Methyl 1-methylcyclododecyl ether | 160 |
| α-Hexylcinnamaldehyde | 120 |
| Benzyl acetate extra | 100 |
| Incense odoresins | 60 |
| Versalide | 60 |
| Terpinol | 60 |

Example C-continued

| Odorant composition | Parts by weight |
|---|---|
| Rhodinol pure | 60 |
| Citral | 40 |
| α-Methylbenzyl acetate | 20 |
| 2-Methyl-4-(2,6,6-trimethyl-2-cyclohexenyl)-3-butenal | 60 |
| | 1000 |

The basic composition, which is reminiscent of the fragrance in the air of forests, takes on more volume by the addition of 2-methyl-4-(2,6,6-trimethyl-2-cyclohexenyl)-3-butenal; it becomes warmer and the slightly dominating note of citral becomes better enveloped.

Example D

| Odorant composition | Parts by weight |
|---|---|
| α-Ionone | 400 |
| α-iso-Methylionone | 200 |
| Phenylethyl alcohol | 200 |
| Δ$^2$-Octynoic acid methyl ester (10% in 95° alcohol) | 40 |
| Rhodinol pure | 20 |
| Geranium oil Bourbon | 20 |
| Heliotropin | 20 |
| ylang-ylang oil extra | 20 |
| 3-Methyl-5-(2,2,6-trimethylcyclohexyl)-4-penten-2-ol | 80 |
| | 1000 |

The basic composition (violet type) becomes flowery by the addition of 3-methyl-5-(2,2,6-trimethylcyclohexyl)-4-penten-2-ol and there is obtained a characteristic sandela note.

What is claimed is:

1. An odorant composition which contains as an odor-imparting ingredient an effective amount of an alcohol of the general formula

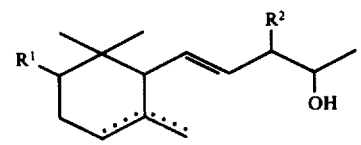

(I)

wherein R$^1$ represents a hydrogen atom or a methyl group and R$^2$ represents a C$_{1-6}$ alkyl group and wherein one of the two additional bonds indicated by dots may be present and at least one other olfactorily desirable agent.

2. An odorant composition in accordance with claim 1, wherein said alcohol is 3-methyl-5-(2,6,6-trimethyl-2-cyclohexenyl)-4-penten-2-ol.

3. An odorant composition in accordance with claim 1, wherein said alcohol is 3-methyl-5-(2,5,6,6-tetramethyl-2-cyclohexenyl)-4-penten-2-ol.

4. An odorant composition in accordance with claim 1, wherein said alcohol is 3-methyl-5-(2,2,6-trimethylcyclohexyl)-4-penten-2-ol.

5. An odorant composition in accordance with claim 1, wherein said alcohol is 3-methyl-5-(2,2-dimethyl-6-methylenecyclohexyl)-4-penten-2-ol.

6. An odorant composition in accordance with claim 1, wherein said alcohol is 3-ethyl-5-(2,6,6-trimethyl-2-cyclohexenyl)-4-penten-2-ol.

* * * * *